(12) United States Patent
Zhao et al.

(10) Patent No.: US 7,211,382 B2
(45) Date of Patent: May 1, 2007

(54) PRIMER EXTENSION USING MODIFIED NUCLEOTIDES

(75) Inventors: Xiaodong Zhao, Bridgewater, NJ (US); Craig A. Gelfand, Jackson, NJ (US); Rolf E. Swenson, Princeton Junction, NJ (US)

(73) Assignee: Orchid Cellmark Inc., Princeton, NJ (US)

( * ) Notice: Subject to any disclaimer, the term of this patent is extended or adjusted under 35 U.S.C. 154(b) by 345 days.

(21) Appl. No.: 10/119,520

(22) Filed: Apr. 9, 2002

(65) Prior Publication Data

US 2003/0190627 A1    Oct. 9, 2003

(51) Int. Cl.
C12Q 1/68 (2006.01)
C12P 19/34 (2006.01)
C07H 21/02 (2006.01)
C07H 21/04 (2006.01)

(52) U.S. Cl. .................. 435/6; 435/91.2; 536/23.2
(58) Field of Classification Search .............. 435/6, 435/91.2, 395; 536/24.33, 23.1, 25.32, 23.2
See application file for complete search history.

(56) References Cited

U.S. PATENT DOCUMENTS

| | | | |
|---|---|---|---|
| 5,595,877 A | 1/1997 | Gold et al. | |
| 5,614,389 A * | 3/1997 | Auerbach | 435/91.2 |
| 5,679,524 A | 10/1997 | Nikiforov et al. | |
| 5,792,607 A | 8/1998 | Backman et al. | |
| 5,817,785 A | 10/1998 | Gold et al. | |
| 5,843,650 A | 12/1998 | Segev | |
| 5,846,710 A * | 12/1998 | Bajaj | 435/6 |
| 5,856,092 A | 1/1999 | Dale et al. | |
| 5,888,819 A | 3/1999 | Goelet et al. | |
| 5,922,574 A | 7/1999 | Minter | |
| 5,952,174 A | 9/1999 | Nikiforov et al. | |
| 6,001,611 A | 12/1999 | Will | |
| 6,004,744 A * | 12/1999 | Goelet et al. | 435/5 |
| 6,013,431 A | 1/2000 | Soderlund et al. | |
| 6,025,133 A | 2/2000 | Stull et al. | |
| 6,060,245 A | 5/2000 | Sorge et al. | |
| 6,090,590 A * | 7/2000 | Kao | 435/91.2 |
| 6,110,710 A | 8/2000 | Smith et al. | |
| 6,130,038 A | 10/2000 | Becker et al. | |
| 6,136,535 A | 10/2000 | Lorincz et al. | |
| 6,200,757 B1 | 3/2001 | Kurn et al. | |
| 6,218,151 B1 | 4/2001 | Cleuziat et al. | |
| 6,238,865 B1 | 5/2001 | Huang et al. | |
| 6,238,868 B1 | 5/2001 | Carrino et al. | |
| 6,245,507 B1 | 6/2001 | Bogdanov | |
| 6,268,490 B1 | 7/2001 | Imanishi et al. | |
| 6,280,952 B1 * | 8/2001 | Weisburg et al. | 435/6 |
| 6,514,768 B1 * | 2/2003 | Guire et al. | 436/518 |
| 6,537,748 B1 | 3/2003 | Goelet et al. | |
| 6,670,461 B1 * | 12/2003 | Wengel et al. | 536/23.1 |
| 2002/0068708 A1 | 6/2002 | Wengel | |
| 2003/0134808 A1 | 7/2003 | Wengel | |
| 2003/0144231 A1 | 7/2003 | Wengel | |

OTHER PUBLICATIONS

Newton et al., Analysis of any point mutation in DNA. The amplification refractory mutation systems (ARMS). Nucleic Acids Res. vol. 17 (7) pp. 2503-2516 (Apr. 11, 1989).

Nguyen, et al, "Minimising the secondary structure of DNA targets by incorporation of a modified deoxynucleoside: implications for nucleic acid analysis by hybridization", Nucleic Acids Research, vol. 28, No. 20, pp. 3904-3909 (2000) Abstract.

Pfundheller, et al., "Evaluation of oligonucleotides containing two novel 2'-O-methyl modified nucleotiede monomers: a 3' -C-allyl and a 2' -O,3'-C- linked bicyclic derivative", Nucleosides Nucleotides vol. 18 No. 9, pp. 2017-2030 Sep. (1999) Abstract.

Zheng, et al., "A simple and efficient method to reduce nontemplated nucleotide addition at the 3 terminus of RNAs transcribed by T7 RNA polymerase". RNA vol. 5, No. 9, pp. 1268-1272, Sep. 1999 (Abstract).

Kao, et al. "Methods: A companion to Methods in Enzymology", vol. 23, No. 3, Mar. 2001 (Abstract).

Kao et al., "A simple and efficient method to transcribe RNAs with reduced 3' heterogeneity", Methods, vol. 23, No. 3, pp. 201-205, Mar. 2001 (Abstract).

Wilds, et al., "2'Deoxy-2'-fluoro-$\beta$-$_D$- arabinonucleosides and oligonucleotides (2'F-ANA): synthesis and physicochemical studes". Nucleic Acids Research, vol. 28, No. 18, pp. 3625-3635, 2000 (Abstract).

Kao, et al., "A simple and efficient method to reduce nontemplated nucleotide addition at the 3 terminus of RNAs transcribed by T7 RNA polyermase" RNA vol. 5, No. 9, pp. 1268-1272, 1999 (Abstract).

(Continued)

Primary Examiner—Kenneth R. Horlick
Assistant Examiner—Joyce Tung
(74) Attorney, Agent, or Firm—William D. Schmidt; Kalow & Springut LLP

(57) ABSTRACT

The present invention provides methods and compositions that reduce target-independent primer extension or enhance template dependent primer extension. The methods and compositions of the present invention are applicable not only in PCR, but also in nucleic acid sequencing, genotyping, and other applications employing extension of a primer in a target-dependent manner.

16 Claims, 7 Drawing Sheets

OTHER PUBLICATIONS

Nikiforov, et al., "Genetic Bit Analysis: a solid phase method for typing single nucleotide polymorphisms", Nucleic Acids Research, vol. 22, No. 20, pp. 4167-4175, 1994.

Cargill, et al. "Characterization of single-nucleotide polymorphisms in coding regions of human genes"., Nature America Inc, sections. 19-34, 1999.

Kramer et al., "Enzymatic Amplification of DNA by PCR: Standard Procedures and Optimization", Current Protocols in Molecular Biology, pp. 15.1.1 to 15.2.1 (1999).

Stump, et al., "The use of modified primers to eliminate cycle sequencing artifacts"., Oxford University Press Nucleic Acids Research, vol. 27, Issue 23, pp. 4642-4648 (1999) (Abstract).

Corey, "48000 fold Acceleration of Hybridization by Chemically Modified Oligonucleotides", J. Am. Chem. Soc., vol. 117, pp. 9373-9374 (1995).

Keller, et al., "Synthesis and hybridization properties of oligonucleotides containing 2'-O-modified ribonucleotides"., Oxford University Press, Nucleic Acids Research, vol. 21, No. 19, pp. 4499-4505, (1993).

Cotten, et al., 2'-O-methyl, 2'-O-ethyl oligoribonuleotides and phosphorothioate oligodeoxyribonuleotides as inhibitors of the *in vitro* U7 snRNP -dependent mRNA processing event. Oxford University Press, Nucleic Acids Research, vol. 19, No. 10 pp. 2629-2635 (1991).

Lesnik, et al., "Oligodeoxynucleotides Containing 2'-*O*-Modified Adenosine: Synthesis and Effects on Stability of DNA:RNA Duplexes", Biochemistry, vol. 32, pp. 7832-7838, (1993).

Zhao, et al., "Immobilization of oligodeoxyribonuleotides with multiple anchors to microchips"., Oxford University Press., Nucleic Acids Research, vol. 29, No. 4, pp. 955-959 (2001).

Pastinen, et al., "A system for specific, High-throughput Genotyping by Allele-specific Primer Extension on Microarrays"., Genome Research, vol. 10, Issue 7, pp. 1031-1042, (2000).

Kool., "Hydrogen Bonding, Base Stacking, and Steric Effects in DNA Replication"., Annu. Rev. Biomol. Struct., vol. 30., pp. 1-22 (2001).

Wetmur et al., PCR Strategies "Nucleic Acid Hybridization and unconventional bases", Academic Press ., pp. 69-83 (1995).

Syvänen., "Solid-Phase Minisequencing as a tool to detect DNA Polymorphism"., Methods in Molecular Biology. vol. 98:Forensic DNA Profiling Protocols., pp. 291-298.

* cited by examiner

```
CTATGACTCTTAGGCC
            ||||
         CCGGATTCTCAGTATC
```

Figure 2

1. CTATGACTCTTAGGCC
2. CTATGACTCTTAGGCC
3. CTATGACTCTTAGGCC
4. CTATGACTCTTAGGCC template        −        +

```
CTATGACTCTTAGGTACC
      ||||||
      CCATGGATTCTCAGTATC
```

Figure 4

5. CTATGACTCTTAGGTACC
6. CTATGACTCTTAGG_T_ACC
7. CTATGACTCTTAGG_G_TACC
8. CTATGACTCTTA_G_GTACC template      −                +

PRIMER EXTENSION USING MODIFIED NUCLEOTIDES

This invention was made, in part, with government support by NIST Advanced Technology Program, award no: 70NANB8H4001. The U.S. Government may have certain rights in this invention.

BACKGROUND OF THE INVENTION

Research in biotechnology directed to sequencing nucleic acids is of major importance and has been used to sequence the human genome, make diagnostic probes, treat diseases and for other research applications. Primer extension plays a major role in conducting this research.

Primer extension has diverse applications, such as, for example, various DNA and RNA sequencing methods, polymerase chain reaction (PCR) applications, cloning, enzymatic synthesis of nucleic acids, polymorphism identification, haplotyping, and multitude of other nucleic acid analysis methods. Over the last decade, minisequencing, or single base extension (SBE) technologies, have been used to identify nucleic acids at particular sites, especially in the field of genomic analysis. SBE has been developed into high throughput processes through multiplexing that allows multiple simultaneous nucleic acid identification. Multiplexing has been extended with the advent of new immobilization chemistries to the scale of nucleic acid microchips, or arrays. Thus, SBE can now be performed where the primers are extended and immobilized on a chip, for example, by tag capture methods where extended primers are captured at known positions on the surface of addressable arrays to identify nucleic acids at particular sites. Many other methods are known in the art that use primer extension to identify nucleic acids. Each of these methods relies on the fidelity, efficiency, and accuracy of the primer extension reaction.

There has been tremendous interest in identifying polymorphic sites across the genome. Of particular interest are single nucleotide polymorphisms (SNPs). SNPs are the most common variations in the human genome, occurring at a frequency of about one in 1,000 base pairs. One method of detecting SNPs is by SBE. In one embodiment of SBE, primers are immobilized on solid supports, such as for example, chips, beads or microspheres. These solid supports may have detectable signals or bear tags that allow easy SNP identification. These detectable signals or tags allow genetic information to be easily sorted by any number of methods, including, for example, electrophoresis, mass, volume, or by applying the tagged beads or microspheres to complementarily tagged arrays. Accordingly, large amounts of information can be analyzed in a single experimental run. However, difficulties can occur in analyzing this information due to signal to background noise. For example, the magnitude of noise relative to the expected signal should be low in order to accurately determine the identity of a polymorphic site with a high degree of precision and accuracy. Noise in such a primer extension assay is often sequence-dependent and primarily results from template-independent primer extension, particularly in platforms employing primers immobilized in close proximity to one another, such as on arrays or chips.

Unwanted primer-primer interactions are a common source of template-independent noise. These interactions may occur between two separate but identical primer molecules, between two portions of a single primer molecule, or between two separate but not identical primer molecules. Types of interactions that commonly generate significant noise are those that allow hybridization to occur between two primers, or within a single primer, so that primer extension occurs in the absence of template or target nucleic acid(s). For example, sometimes a single primer molecule can fold into a hairpin structure, resulting in the outcome that the primer also acts as its own template. Alternatively, two primers may interact sufficiently well so that one is capable of serving as template for the other. This results in spurious signal generation because extension of the primer occurs independent of the target nucleic acid sequence.

Attempts have been made to reduce or eliminate unwanted primer interactions by conducting hybridization at elevated temperatures. However, on micro-arrays, primer interactions are more difficult to overcome because primers are immobilized to the surface of the array or chip in very close proximity to one another and array-based protocols may not allow for elevated temperature. Further, temperature effects would tend to disperse primers spatially, but array technologies are based on localized immobilization of the primers, and so spatial separation, by definition, is contradictory to the definition of arrays.

In the case of primer extension in thermal cycling, such as by a thermostable polymerase in PCR, multiple factors are optimized in order to obtain a desired outcome and reduce the likelihood of undesirable primer-primer interactions. For example, varying magnesium chloride concentrations, employing stabilizing additives such as dimethyl sulfoxide, glycerol, formamide, betaine, ammonium sulfate, or commercial or proprietary enhancers, stabilizers, and hybridizing agents are some approaches aimed at minimizing unfavorable primer-primer interactions, or mispriming events, as well as manipulation of reaction conditions such as pH, buffers, ionic and non-ionic detergents and surfactants. Optimization kits are commercially available that aid users in manipulating these factors to some extent. However, multiple factors must be optimized, which can result in costly and time-consuming optimization trials, and certain optimization conditions my not be compatible with array technologies and methods. Further, higher multiplexing levels will only exacerbate sequence-dependent and sequence-independent noise issues, rendering such optimization efforts increasingly difficult—if not impossible—to achieve by biochemical means alone.

Other attempts to avoid primer-primer interactions involve hot start PCR methods. Some hot start methods include inhibition of polymerase by low temperature, or adding polymerase after the melting and annealing step. Hot start PCR improves specificity, sensitivity and yield of the PCR reaction. Other methods avoid nonspecific, or target-independent primer extension by omitting, inhibiting, or sequestering the thermostable polymerase in the initial denaturation and annealing reaction, such as by reversibly binding to the polymerase an inactivating antibody.

Primer self-complementarity also adds to unwanted target-independent extension resulting in inaccurate primer extension and noise. Self-complementarity is the ability of a primer to self-anneal or anneal with another copy of itself. Although self-complementarity can be highly undesirable, it may not be possible to avoid every instance of self-complementarity in primer design for a variety of reasons. For example, the target nucleic acid may contain regions or repetitive stretches of self-complementarity, and thus amplification or primer extension might require primer structure reflecting these repetitive regions.

There are many computer programs used in primer design that limit use of primers that exhibit self-complementarity, or limit the degree of self-complementarity. However, such programs may not be useful in the situation where the target sequence for which the primer is being synthesized bears a region of self-complementarity. For example, if a target nucleic acid molecule has a sequence that requires the use of primers having a palindromic sequence at its 3' terminus, such as for example a restriction site, self-complementarity might not be avoided.

Palindromes are sequences that symmetric. That is, they read the same from the 5' to 3' direction as they read from the 3' to 5' direction. One characteristic of a palindromic sequence is that it is self-complementary, and thus generally able to hybridize to itself, or other copies of itself. In the case that a palindrome is at the 3' terminus of the primer, it can hybridize with the 3' terminus of another primer molecule that is acting as template, confounding attempts to extend the primer employing the target nucleic acid as a template. Generally, the closer a region of self-complementarity is to the 3' end of a primer, the more likely it is to interfere with primer extension. Efforts can be made to minimize the likelihood of interference, such as maintaining short primers 30 to 40 nucleotides in length, and matching thermodynamic parameters for primers. However, this is not always a viable solution due, to constraints set by the sequences of the target nucleic acid, as discussed above.

Physical separation of an essential reaction component prior to the first denaturation step can often reduce target-independent priming. Denaturation of target nucleic acid before the addition of a polymerizing agent or magnesium chloride can improve the specificity and sensitivity of the primer extension reaction, but requires an added step where tubes are reopened to add the missing component. This added step becomes unwieldy when running a multitude of samples.

Other attempts to reduce target-independent primer extension employ reversible inhibition of the polymerizing agent by, for example, an antibody, which can be effective in some circumstances. However, this approach is more expensive and time consuming and requires an added step, which is undesirable when running a multitude of samples.

Enhancers can be employed to increase yield, specificity and the likelihood of overcoming high GC content or long templates. Such enhancers include compounds which often can increase yield, such as nonionic detergents like, for example, Tween-20, or enzyme-stabilizing agents such as bovine serum albumin, or other compounds such as betaine, glycerol, dimethyl sulfoxide, polyethylene glycol, or salts. Improvements in specificity can be achieved through addition of formamide to the reaction mixture, which tends to destabilize mismatched primers.

Target-independent primer extension may occur not only with heat-stable polymerases in a polymerase chain reaction, but in any application employing primer extension on a target nucleic acid. Such applications include those for nucleic acid sequencing, genotyping, and a host of other primer extension methods.

Based on the foregoing, there is a need for methods and compositions that allow primer extension reactions to run maximally with respect to key parameters, such as efficiency, fidelity, accuracy, and high signal-to-noise ratio. The present invention addresses this need and provides methods and compositions that reduce target-independent primer extension or enhance template dependent primer extension. The methods and compositions of the present invention are applicable not only in PCR, but also in nucleic acid sequencing, genotyping, and other applications employing extension of a primer in a target-dependent manner.

SUMMARY OF THE INVENTION

The present invention provides compositions and methods for inhibiting template-independent primer extension or enhancing template dependent primer extension.

In one embodiment, the present invention provides methods for inhibiting template-independent primer extension comprising employing a primer extension reaction using a primer having one or more modified nucleotides, under suitable conditions for primer extension, wherein the primer inhibits template-independent primer extension.

In another embodiment, the present invention provides methods for inhibiting template-independent primer extension comprising employing a primer extension reaction using a primer having one or more modified nucleotides, under suitable conditions for primer extension, wherein each of the one or more modified nucleotides of the primer is modified at the 2' position so that template independent primer extension is inhibited.

In yet another embodiment, the present invention provides a method for identifying one or more nucleotide bases of a target nucleic acid sequence comprising the steps of (a) hybridizing the target nucleic acid sequence with a primer having one or more modified nucleotides, wherein each of the one or more modified nucleotides of the primer is modified at the 2' position so that template independent primer extension is inhibited; (b) extending the primer at the 3' end with one or more nucleotide bases using the one or more nucleotide bases to be identified of the target as a template; and (c) detecting the extended primer, thereby identifying the one or more nucleotide bases of the target nucleotide sequence.

In still yet another embodiment, the present invention provides a method of enhancing template-dependent primer extension, comprising employing a primer extension reaction using a primer having one or more modified nucleotides under suitable conditions for primer extension, wherein the primer enhances template-dependent primer extension.

For a better understanding of the present invention together with other and further advantages and embodiments, reference is made to the following description taken in conjunction with the examples, the scope of which is set forth in the appended claims.

DESCRIPTION OF THE FIGURES

Preferred embodiments of the invention have been chosen for purposes of illustration and description, but are not intended in any way to restrict the scope of the invention. The preferred embodiments of certain aspects of the invention are shown in the accompanying figures, wherein:

FIG. 2 illustrates primer employed in primer extension reactions employing modified and unmodified 16-mer primers. These 16-mer primers (SEQ ID Nos. 10–11) bearing the palindromic sequence 5'-GGCC-3' may anneal with one another. Experiments using these primers are illustrated in FIG. 3.

FIG. 4 illustrates primer extension reactions employing modified and unmodified 18-mer primers. Shown are the 18-mer primers having the palindrome-like sequence 5'-GGTACC-3' that may anneal with one another (SEQ ID Nos. 15–16). Results employing these primers are illustrated in FIG. 5.

FIG. 6 illustrates primer extension reactions using modified and unmodified 20-mers. Shown are the 20-mer primers having the palindrome-like sequence 5'-TATTTG-GAAAATA-3' that may anneal with one another (SEQ ID Nos. 20–21). Results employing this primer are illustrated in FIG. 7.

FIG. 11 illustrates that when the modification is made at the 5'-residue of the region of palindromic-like sequence, template-independent primer extension (−) is inhibited, but not template-dependent primer extension (+).

DETAILED DESCRIPTION OF THE INVENTION

Figure 1:
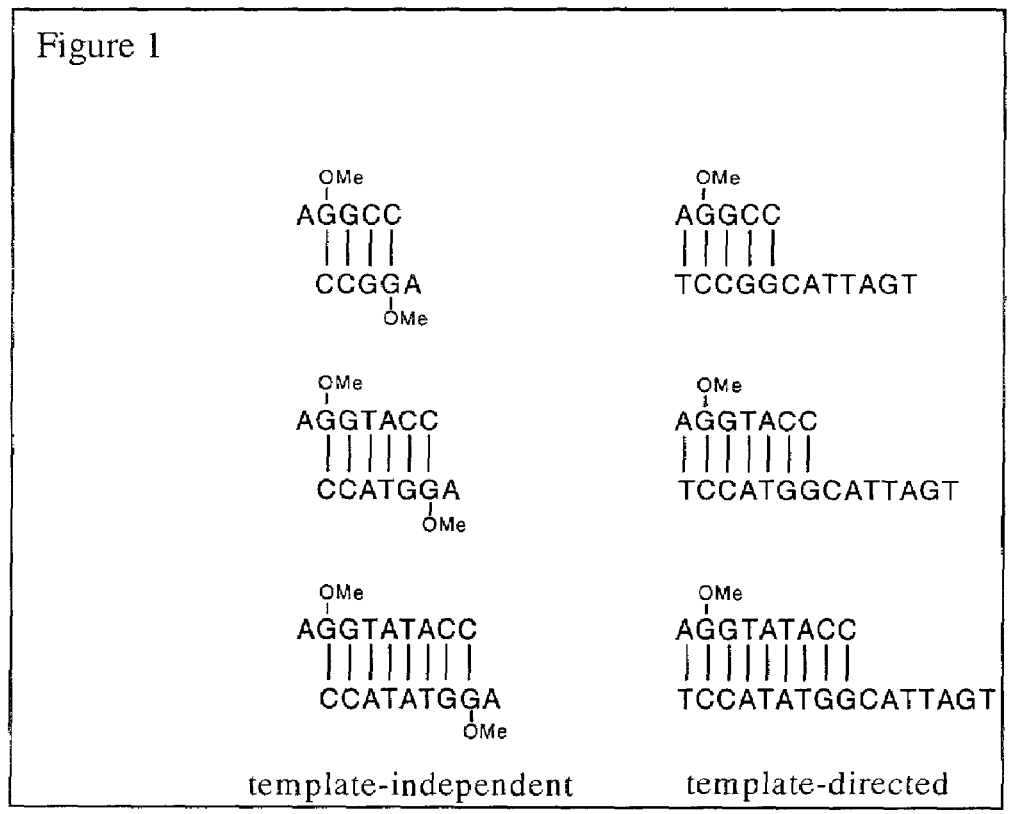
FIG. 1 illustrates difference in duplexes between a self-priming interaction of modified primer and priming between a modified primer (SEQ ID Nos. 1–6) and unmodified template (SEQ ID Nos. 7–9). Formation of primer-primer duplexes, where primers have modifications at or near the 5'-side of palindromic or palindrome-like sequences, yield duplexes with modifications at both 5'-ends of the region of palindromic or palindrome-like sequence. In this experiment, modification at the 2' position on both strands, at or near the 5'-portion of the region of a palindromic or palindrome-like sequence, appears to be responsible for inhibiting extension of a primer interacting with another molecule of the same primer as template. The unmodified standard template, which bears the same palindromic or palindrome-like sequence, although unmodified, supports extension of the primer. Thus, template-directed primer extension in this experiment occurs when at least one strand of the duplex between primer and template is not modified at the 2' position of sugars for the bases or near the 5'-end of the region of palindromic or palindrome-like sequence.

The present invention provides methods and compositions that reduce target-independent primer extension or enhance template dependent primer extension. The methods and compositions of the present invention are applicable not only in PCR, but also in nucleic acid sequencing, genotyping, and other applications employing extension of a primer in a target-dependent manner.

Primer Extension

The present invention can be employed in any primer extension reaction where the primer is intended to be extended or otherwise lengthened, such as for example by ligation, in a template-dependent manner. Primer extension includes extension of one or more primers, by one or more nucleotides or modified nucleotides. Primer extension methods are well known in the art. Some primer extension methods include, but are not limited to, PCR, the ligase chain reaction, oligonucleotide ligation assays, other ligation reactions, rolling circle amplification, ARMS (amplification refractory mutation system), and the like.

Suitable conditions for primer extension are readily determined by those skilled in the art. These conditions include incubation temperature, incubation time, assay reagents, stabilizing factors, polymerizing agent, pH, and ionic strength sufficient to promote base pairing between the primer and desired template or target sequence. Polymerizing agents include agents capable of extending a primer by adding or substituting a nucleotide or modified nucleotide at the 3' end of the primer. Suitable polymerizing agents include all manner of nucleotide polymerases. Among preferred polymerases are DNA polymerases, particularly those lacking exonuclease activity, such as, for example, the exonuclease deleted Klenow fragment of DNA polymerase.

Polymerizing agents may be isolated or cloned from a variety of organisms including viruses, bacteria, archaebacteria, fungi, mycoplasma, prokaryotes, and eukaryotes. Polymerases exhibiting thermal stability may also be employed, such as for example, polymerases from *Thermus* species, including *Thermus aquaticus, Thermus thermophilus*, and *Thermus flavus; Pyrococcus* species, including *Pyrococcus furiosus, Pyrococcus* sp. GB-D, and *Pyrococcus woesei, Thermococcus litoralis*, and *Thermogata maritime*. Biologically active proteolytic fragments, recombinant polymerases, genetically engineered polymerizing enzymes, and modified polymerases are included in the definition of polymerizing agent. It should be understood that the invention can employ various types of polymerases from various species and origins without undue experimentation.

Suitable conditions for primer extension include hybridization and stringency conditions allowing desired hybridization between the primer and template or target sequence. As used herein, two nucleic acid sequences are said to be capable of specifically hybridizing to one another if the two molecules are capable of forming an anti-parallel, double-stranded nucleic acid structure or hybrid under hybridizing conditions, whereas they are substantially unable to form a double-stranded structure or hybrid when incubated with a non-target nucleic acid sequence under the same conditions. A nucleic acid molecule is said to be the "complement" of another nucleic acid molecule if it exhibits complete Watson-Crick base pair complementarity. As used herein, nucleic acid molecules are said to exhibit "complete complementarity" when every nucleotide of one of the molecules is complementary to a nucleotide of the other. Two molecules are said to be "substantially complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Typically, high stringency conditions include conditions selected to be 5 or more degrees higher than the thermal melting point (Tm) for a specific sequence at a defined ionic strength and pH. The Tm is the temperature (under defined ionic strength and pH) at which 50% of the target sequence hybridizes to a perfectly matched sequence. Stringency conditions in referring to homology or substantial similarity in the hybridization context, can be combined conditions of salt, temperature, organic solvents or other parameters that are typically known to influence hybridization. These techniques are well known in the art. For example, conventional stringency conditions are described, for example, by Sambrook, J., et al., in *Molecular Cloning, a Laboratory Manual, 2nd Edition*, Cold Spring Harbor Press, Cold Spring Harbor, N.Y. (1989), and by Haymes, B. D., et al. in *Nucleic Acid Hybridization, A Practical Approach*, IRL Press, Washington, D.C. (1985), both herein incorporated by reference).

One preferred primer extension reaction that is useful for detecting polymorphic sites is SNP-IT™. This type of primer extension reaction (disclosed by Goelet, P. et al. in U.S. Pat. Nos. 5,888,819 and 6,004,744, each herein incorporated by reference in its entirety) is a preferred method for determining the identity of a nucleotide at a predetermined polymorphic site in a target nucleic acid sequence. Thus, it is uniquely suited for SNP genotyping, although it also has general applicability for determination of a wide variety of polymorphisms. SNP-IT™ is a method of polymorphic site interrogation in which the nucleotide sequence information surrounding a polymorphic site in a target nucleic acid sequence is used to design an oligonucleotide primer that is complementary to a region immediately adjacent to the 3' end of the target polynucleotide, but not including the variable nucleotide(s) in the polymorphic site of the target polynucleotide. The target polynucleotide is isolated from a biological sample and hybridized to the interrogating primer. Following isolation, the target polynucleotide may be amplified by any suitable means prior to hybridization to the interrogating primer. The primer is extended by a single labeled terminator nucleotide, such as a dideoxynucleotide, using a polymerase, often in the presence of one or more chain terminating nucleoside triphosphate precursors (or suitable analogs). A detectable signal is thereby produced. As used herein, the length of the primer used includes sequence beginning from the base immediately adjacent to the polymorphic site to as many as 100 nucleotides or more, more preferably a length extending to about 10 to about 25 nucleotides in the 5' direction, on either strand, of the polymorphic site. Most preferably, the primer is hybridized one nucleotide immediately adjacent to the polymorphic site in either the 3' or 5' direction.

In some embodiments of SNP-IT™, the primer is bound to a solid support prior to hybridization and the extension reaction. In other embodiments, the extension reaction is performed in solution (such as in a test tube or a micro well) and the extended product is subsequently bound to a solid support. In an alternate embodiment of SNP-IT™, the primer is detectably labeled and the extended terminator nucleotide is modified so as to enable the extended primer product to be bound to a solid support. An example of this includes where the primer is fluorescently labeled and the terminator nucleotide is a biotin-labeled terminator nucleotide and the solid support is coated or derivatized with avidin or streptavidin. In such embodiments, an extended primer would thus be capable of binding to a solid support and non-extended primers would be unable to bind to the support, thereby producing a detectable signal dependent upon a successful extension reaction.

Ligase/polymerase mediated genetic bit analysis (U.S. Pat. Nos. 5,679,524, and 5,952,174, both herein incorporated by reference) is another example of a suitable polymerase-mediated primer extension method for determining the identity of a nucleotide at a polymorphic site. Ligase/polymerase SNP-IT™ utilizes two primers. Generally, one primer is detectably labeled, while the other is designed to be affixed to a solid support. Alternatively, the reaction can be performed in solution, with one of the primers bearing a moiety facilitating subsequent immobilization, either by nucleic acid hybridization or haptenation as with biotin. In alternate embodiments of ligase/polymerase SNP-IT™, the extended nucleotide is detectably labeled. The primers in ligase/polymerase SNP-IT are designed to hybridize to each side of a polymorphic site, such that there is a single base gap comprising the polymorphic site. Only a successful extension reaction, followed by a successful ligation reaction, enables production of the detectable signal.

An alternate primer extension method for determining the identity of a nucleotide at a polymorphic site in a target polynucleotide is described in Söderlund et al., U.S. Pat. No. 6,013,431 (the entire disclosure is herein incorporated by reference). In this method, the nucleotide sequence surrounding a polymorphic site in a target nucleic acid sequence is used to design an oligonucleotide primer that is complementary to a region flanking the 3' or 5' end of the target polynucleotide, but not including the variable nucleotide(s) in the polymorphic site of the target polynucleotide. The target polynucleotide is isolated from the biological sample and hybridized with an interrogating primer. In some embodiments of this method, following isolation, the target polynucleotide may be amplified by any suitable means prior to hybridization with the interrogating primer. The primer is extended, using a polymerase, often in the presence of a mixture of at least one labeled deoxynucleotide and one or more chain terminating nucleoside triphosphate precursors (or suitable analogs). A detectable signal is produced on the primer upon incorporation of the labeled deoxynucleotide into the primer. Other methods of primer extension suitable for use in the present invention are disclosed in Dale et al. U.S. Pat. No. 5,856,092 (the entire disclosure is herein incorporated by reference). Dale et al. disclose primer extension and capture using one or more separation elements.

Preferred primer extension reactions of the present invention employ a mixture of one or more nucleotides and a polymerizing agent. The term "nucleotide" or nucleic acid as used herein is intended to refer to ribonucleotides, deoxyribonucleotides, acylic derivatives of nucleotides, and functional equivalents or derivatives thereof, including any phosphorylation state capable of being added to a primer by a polymerizing agent. Functional equivalents of nucleotides are those that act as substrates for a polymerase as, for example, in an amplification method. Functional equivalents of nucleotides are also those that may be formed into a polynucleotide that retains the ability to hybridize in a non-disruptive, or preferably, a sequence-specific manner to a target polynucleotide. Examples of nucleotides include chain-terminating nucleotides, most preferably dideoxynucleoside triphosphates (ddNTPs), such as ddATP, ddCTP, ddGTP, and ddTTP; however other terminators known to those skilled in the art, such as acyclonucleotide analogs or arabinoside triphosphates, are also within the scope of the present invention. These analogs differ from conventional 3' deoxynucleoside triphosphates (dNTPs) in that, minimally, they lack a hydroxyl group at the 3' position of the sugar component, or are structural variants lacking the traditional sugar geometry in part or entirely.

The nucleotides employed in the primer extension reaction may bear a detectable characteristic. As used herein a detectable characteristic includes any identifiable characteristic that enables distinction between nucleotides. It is important that the detectable characteristic does not interfere with any of the methods of the present invention. Detectable characteristic refers to an atom or molecule or portion of a molecule that is capable of being detected employing an appropriate method of detection. Detectable characteristics include inherent mass, electric charge, electron spin, mass tags, radioactive isotopes, dyes, bioluminescent moieties, chemiluminescent moieties, nucleic acid moieties, haptens, proteins, light scattering/phase shifting moieties, or fluorescence moieties.

Nucleotides and primers may be labeled according to any technique known in the art. Preferred labels include radiolabels, fluorescent labels, enzymatic labels, proteins, haptens, antibodies, sequence tags, mass tags, fluorescent tags and the like. Preferred dye type labels include, but are not limited to, TAMRA (carboxy-tetramethylrhodamine), ROX (carboxy-X-rhodamine), FAM (5-carboxyfluorescein), and the like.

Target Nucleic Acids

The present invention provides methods of extending primers using a target nucleic acid sequences as the desired template. The target nucleic acid sequence will preferably be biologically active with regard its capacity to hybridize, or form a duplex, with another nucleic acid, oligonucleotide, or polynucleotide molecule. Target nucleic acid sequences may be DNA, RNA, hybrids, chimeras, or other nucleic acid molecules. The target may be single-stranded, double-stranded, or DNA/RNA hybrid duplex. Target nucleic acid sequences may be polynucleotides or oligonucleotides. Preferred target nucleic acid sequences are between 40 to about 200 nucleotides in length, in order to facilitate detection. The target nucleic acid sequence can be cut or fragmented into these segments by methods known in the art, for example, by mechanical or hydrodynamic shearing methods such as sonication, or by enzymatic methods such as restriction enzymes or nucleases. Target nucleic acid sequences may be derived from any source, either natural or synthetic, and may contain unnatural or modified nucleotides, nucleotide analogs, linkers, labels, tags, universal bases or abasic residues.

In a preferred embodiment, the target nucleic acid may be isolated, or derived from a biological sample. The term "isolated" as used herein refers to the state of being substantially free of other material such as non-nuclear proteins, lipids, carbohydrates, or other materials such as cellular debris or growth media with which the target nucleic acid may be associated. The term "isolated" is not intended to refer to a complete absence of these materials. Neither is the term "isolated" generally intended to refer to the absence of stabilizing agents such as water, buffers or salts, unless they are present in amounts that substantially interfere with the methods of the present invention. It should be noted, however, that the methods of the present invention do not require the target nucleic acids to be isolated or substantially free of other material, as long as conditions suitable for primer extension are maintained. The term "sample," as used herein, refers to any material containing nucleic acid molecules, such as for example, DNA, RNA or DNA/RNA hybrids or chimeras. Samples may be derived from any source, including plants and animals and materials obtained therefrom. Preferably, samples will be in the form of blood samples, tissue samples, cells directly from individuals or propagated in culture, plants, yeast, fungi, mycoplasma, viruses, viroids, archaebacteria, histology sections, or buccal swabs, for example, all either fresh, fixed, frozen, embedded in paraffin or in another fixative.

Preferably, the target nucleic acids are from genomic DNA drawn from a diverse population of humans so as to conduct genotyping, genetic mapping, or other studies relating to genetics or genomics. Such genomic DNA preferably includes one or more polymorphic sites and is used to amplify a region encompassing the one or more polymorphic sites through an amplification method, such as for example, PCR. The PCR reactions can be run individually, or, preferably, in a multiplexed fashion, where 2 to hundreds or more polymorphic sequences from one or more individuals are amplified simultaneously in the same reaction vessel. The amplified regions are then preferably further genotyped by, for example, single base extension employing one or more of the methods of the present invention.

It should be noted that, although target nucleic acids preferably contain at least one polymorphism, and the methods of the present invention may be carried out in genotyping studies, the present invention is not limited to the field of genotyping. The methods of the present invention may be employed in the context of any process wherein a primer is to be extended in a template-dependent manner. Accordingly, the PCR reaction itself can also benefit from the present invention, as PCR is a common form of template-dependent primer extension. Ligation reactions also can be enhanced, as many ligases that operate in double-stranded nucleic acids also function in a template-dependent manner to link specifically two primers or other DNA strands together.

The target nucleic acid sequences or fragments thereof may, but not necessarily, contain polymorphic site(s), or include such site(s) and sequences located either distal or proximal to the sites(s). These polymorphic sites or mutations may be in the form of deletions, insertions, re-arrangement, repetitive sequence, base modifications, or base changes at a particular site in a nucleic acid sequence. This altered sequence and the more prevalent, or normal, sequence may co-exist in a population. In some instances, these changes confer neither an advantage nor a disadvantage to the species or individuals within the species, and multiple alleles of the sequence may be in stable or quasi-stable equilibrium. In some instances, however, these sequence changes will confer a survival or evolutionary advantage to the species, and accordingly, the altered allele may eventually over time be incorporated into the genome of many or most members of that species. In other instances, the altered sequence confers a disadvantage to the species, as where the mutation causes or predisposes an individual to a genetic disease or defect. As used herein, the terms "mutation" or "polymorphic site" refers to a variation in the nucleic acid sequence between some members of a species, a population within a species or between species. Such mutations or polymorphisms include, but are not limited to, SNPs, multiple base polymorphisms, one or more base deletions, or one or more base insertions.

Primers

The present invention may utilize one or more primers. In order for an oligonucleotide to serve as a primer, it typically need only be sufficiently complementary in sequence to be capable of forming a double-stranded structure with the target sequence under the conditions employed. The term "primer" refers to a specific oligonucleotide or polynucleotide, which is capable of acting as a point of initiation of synthesis when employed under conditions in which synthesis of a primer extension product that is complementary to a specific template or target nucleic acid sequence is desired. Synthesis in this case also includes any formation of a new phosphodiester bond to the end of such a primer, as in, for example, ligation reactions.

Preferred primers of the present invention include oligonucleotides from about 8 to about 40 nucleotides in length, to longer polynucleotides that may be up to several thousand nucleotides long. Short primers generally require higher temperatures under a given set of conditions to form sufficiently stable hybrid complexes with a template. Most preferably, oligonucleotides synthesized to be used as primers are generally at least 10 to about 25 nucleotides long, assuring a sufficient level of hybridization specificity.

Primers of the present invention can have various nucleic acid residues, such as for example, an unmodified residue, a terminating residue (labeled or unlabeled), it may bear a modification, or any other feature as long as the polymerizing agent is capable of functioning on the primer as a viable substrate.

Primers of the present invention include one or more modified nucleotides capable of incorporation into a primer in the place of a ribosyl or deoxyribosyl moiety. As used herein, modified nucleotides include any modification at the 2' position of sugar moiety of the nucleoside. Preferred modifications at the 2' positions include substituted, unsubstituted, saturated, unsaturated, aromatic or non-aromatic moieties. Suitable moieties at the 2' position include, but are not limited to, alkoxy (such as methoxy, ethoxy, propoxy), 2'-oxy-3-deoxy, 2'-t-butyldimethylsilyloxy, furanyl, propyl, pyranosyl, pyrene, acyclic moieties, and the like. More preferred modifications include a substituted and unsubstituted hydrocarbon moiety, where the bond from the 2'-carbon is a carbon-carbon bond. The most preferred modification is a methoxy moiety, attached to the 2'-carbon by a carbon-oxygen bond.

In one embodiment of the present invention, one modified nucleotide comprises a methoxy group at the 2' position of the nucleotide. However, as discussed above, the present invention includes other modifications.

The primer can have one or more modified nucleotides.

Template-Dependent and Template-Independent Primer Extension

A primer having one or modified nucleotides is employed in a primer extension reaction where template-dependent primer extension is desired. Preferably, the one or more modified nucleotides enhance template-dependent primer extension and/or inhibit template independent primer extension. Template-dependent primer extension includes the extension of a primer in accordance with the sequence of a desired template nucleic acid molecule. Preferably, the primer must be sufficiently homologous to the desired template in order that it may adhere or anneal to the template sufficiently to support extension of the primer by a nucleic acid residue, or base, whose identity is determined by the sequence of the desired template.

Template-independent primer extension may occur by a primer hybridizing to itself and being acted upon by a polymerizing agent. One example of such hybridization is the presence of sequences on a primer that are palindromes or palindrome-like, as described herein.

Palindromic nucleic acid sequences are those that are symmetric. Typically, they exhibit a two-fold axis of symmetry; a plane placed at a position within a sequence will reveal that the left side of the sequence is a mirror image of the right side of the sequence, when reading the sequence from the opposite strand. The tendency to be palindromic is encoded in the base sequence of a single strand, but, often the visual recognition of palindromic sequences is only apparent when viewing the sequence with both strands of a duplex represented. Palindrome-like sequences bear some palindromic character, in that portions of them may exhibit the symmetry discussed above, but that symmetry can be broken by one or a stretch of nucleic acid residues. For purposes of the present invention, a primer P capable of annealing to itself, or another molecule of itself, or another molecule having a region of sufficient homology to hybridize to the same primer sequence, either intramolecularly or between two identical primer molecules under the conditions for polymerizing agent activity, should be considered to bear a palindrome-like sequence. The present invention can be employed in palindrome or palindrome-like sequences, by placing a 2'-modification, or other equivalent analog, at or near the 5'-end of the palindromic or palindrome-like region, deterring the polymerization event without necessarily altering the duplex stability that would otherwise lead to the incorrect polymerization.

Enhancement of template-dependent primer extension includes any improvement in the signal-to-noise ratio, with reference to the signal generated by extension of a primer on a desired target nucleic acid or nucleotide or region thereof. Confounding signal generated by template-independent or undesirable template-dependent polymerization constitutes unwanted "noise" in assays where it is desirable to generate a signal only in a template-dependent and target-dependent manner, employing a target nucleic acid of interest as a template. Enhanced template-dependent primer extension includes increases in the ratio between the expected signal to noise signal, compared to such a ratio resulting from primer extension without using modified nucleotides. Enhancement includes increases in signal of preferably from about less than one-fold to two- or more-fold, more preferably, from about two-fold to about a hundred-fold, and most preferably, from about 2-fold to about a thousand-fold or higher over primer extension using primers with no modification.

Where primers may be extended in accordance with sequences other than those in desired target nucleic acids, unwanted noise may be generated. The methods of the present invention reduce such noise, and thus improve the signal-to-noise ratio, resulting in an enhancement of template-dependent primer extension signal generated from the target nucleic acid(s) of interest. Signal-to-noise ratios may be highly unfavorable in certain situations, such as in multiplexed samples or samples on arrays. Employing the invention in these situations can lead to a significant enhancement of the signal for template-dependent primer extension.

Inhibition of non-target-dependent primer extension includes inhibiting undesired template-dependent or template-independent primer extension. Preferably there is 100% inhibition of template-independent extension. However, inhibition includes a decrease in signal as a result of template-independent primer extension by preferably from about 1% to about 100%, more preferably, from about 50% to about 80%, and most preferably, from about 70% to about 90% inhibition or higher over primer extension using primers with no modification.

In one embodiment, the present invention can be employed where a target nucleic acid sequence has repetitious sequences, or one or more sequences of sufficient homology to the primer, and the primer is desired to be extended employing a particular region having repetitive sequences to the exclusion of other regions having similar repetitive sequences. In such an embodiment, both the primer and elements of the undesired homologous sequence in the undesired regions may be modified so as to prevent undesired primer extension, in accordance with the invention described herein. Thus, the present invention encompasses embodiments where the target nucleic acid may be modified to include one or more modified nucleotides, the primers bear one or more modifications or combinations thereof, inhibiting both primer extension based on primer sequences and primer extension based on undesired sequences in the target nucleic acid similar to the primer sequences.

Solid Support

The primers or target nucleic acids of the present invention may be bound to any solid support known in the art. Solid supports include rigid, semi-rigid, or gel-like substances that can be made to immobilize molecules or compounds of interest, such as, for example, a nucleic acid molecule. These substances may include agar, agarose, cellulose, cellulose derivatives such as, for example, nitrocellulose, glass, varieties of glasses, controlled pore glass, silica, silica gel, silane-coated surfaces, plastics, such as, for example, polypropylene and polystyrene, nylon, and inorganic and organic polymers. The solid support may be in any geometric conformation, including two- and three-dimensional surfaces. The support may be contiguous, or may be particulate, such as microspheres or beads that are substantially uniform or spherical or adopt any other shape or combination of shapes, such as toruses or cubes, for example. The support may be capable of forming a suspension in a liquid or gel medium. Other properties may be combined with the support, such as coating magnetic or intrinsically fluorescent materials with support material.

Where the support is noncontiguous, such as for particulates, individual particulates may bear identifiable characteristics, such that populations of support-bearing particulates may be identified by one or more characteristics of individual particles. Solid supports, includes arrays, addressable arrays, and virtual arrays. Arrays include ordered arrangement of components, such as, for example, primers. Addressable arrays include an ordered arrangement of components whereby the placement of each component on a solid support is known by some coordinate system. Virtual arrays include a collection or suspension of particulates coated with a solid support wherein the solid support-coated particulates bear unique identifying characteristics in addition to a moiety of interest, for example, a primer, and where individual particulate components within a particulate mixture are capable of being identified or even physically separated by virtue of their unique characteristic(s) and by the nature of the moiety of interest thereto attached, for example, a primer. Identifiable characteristics associated with such particulates include, for example, diameter, density, size, color, and the like. Arrays also include what are commonly referred to in the art as "chips," "DNA chips," "DNA microchips," "microchips," and the like.

Preferred arrays for the present invention include, but are not limited to, addressable arrays including an array as defined above wherein individual positions have known coordinates such that a signal at a given position on an array may be identified as having a particular identifiable characteristic. One particularly preferred array is the GenFlex™ Tag Array, from Affymetrix, Inc., that has capture probes for 2,000 tag sequences. These are 20 mer oligonucleotides selected to have similar hybridization characteristics and at least minimal homology to other members of the 2,000 tag set.

Another preferred array is the addressable array that harbors sequences complementary to the unique tags of the affinity probes. These sequences are bound to the array at known positions. This type of tag hybridizes with the array under suitable hybridization conditions. By locating signal on the surface of the array, the nucleotide identity at the polymorphic site can be determined. In one preferred embodiment of the present invention, the target nucleic acid sequences are arranged in a format that allows multiple simultaneous detections (multiplexing), as well as parallel processing using oligonucleotide arrays.

In another embodiment, the present invention includes virtual arrays where extended and unextended affinity probes are separated on an array where the array comprises a suspension of microspheres, where the microspheres bear one or more capture moieties to separate the uniquely tagged primers. The microspheres, in turn, bear unique identifying characteristics such that they are capable of being separated on the basis of that characteristic, such as for example, diameter, density, size, color, and the like. Solid supports may also be formed, for example, into wells (as in 96-well dishes), plates, slides, sheets, membranes, fibers, chips, dishes, and beads. In certain embodiments of the present invention, the solid support is treated, coated, or derivatized so as to facilitate the immobilization of the affinity probe or a target nucleic acid sequence. Preferred treatments include coating, treating, or derivatizing with poly-L-Lys, streptavidin, antibodies, silane derivatives, low salt, or acid.

Compositions

The present invention provides genotyping, haplotyping, and diagnostic compositions including kits having primers having a nucleotide modified at the 2' position. These primers may be tagged or untagged. The kit may also include one or more containers, as well as additional reagent(s) and/or active and/or inert ingredient(s) for performing any variations on the methods of the invention. Exemplary reagents include, without limitation, at least two or more primers having modified or unmodified nucleotides, one or more terminator nucleotides, such as dideoxynucleotides, that are labeled with a detectable marker, and one or more polymerases or other polymerizing agents. The kits can also include instructions for mixing or combining ingredients or use. The kits can include primers bound to a solid support.

Preferred kits of the invention include primers having a palindromic region at the 3' terminus and a single 2'-modified nucleic acid residue in the primer where the single 2'-modified nucleic acid residue is the initial residue of the 5' end of the palindromic region. This region is immediately adjacent to the upstream residue from the 5' end of the palindromic region, the second residue upstream from the 5' end of the palindromic region, or the third residue upstream from the 5' end of the palindromic region. Upstream from the palindromic region refers to the 5' direction, such that when a primer sequence is viewed horizontally displayed with the 5' terminus on the left and the 3' terminus on the right, upstream refers to residues on the left of the palindromic region. Preferred embodiments of the invention include such primers as described above, wherein the palindromic region is four to ten nucleotides in length.

Having now generally described the invention, the same may be more readily understood through the following reference to the following examples, which are provided by way of illustration and are not intended to limit the present invention unless specified.

EXAMPLES

Examples 1–4 describe methods of preventing template-independent base extension on DNA chips. One single base modification (MeO-RNA modification) was placed at 5' upstream or at 5' base of the palindrome, or sequence containing secondary structure, of the primer 3'-terminus. This design can abolish base extension on the bridged primer complex, but allows base extension in the presence of template.

Example 1

Arraying 5'-Disulfide-Modified Oligonucleotides to Mercaptosilane-Coated Slides

Oligonucleotides were purchased from Operon. TAMRA-labeled dideoxyribonucleotide triphosphates were purchased from NEN. Klenow Fragment of *E. coli* Pol I was purchased from New England Biolab. The microscope slides (25×75 mm, VWR) coated with mercaptopropylsilane were prepared by methods known in the art. The oligonucleotides were dissolved in arraying buffer (500 mM $Na_2CO_3$, 0.02% SDS, pH 9.6) at 20 µM. Primers were printed at 20 µM on the slides with a Cartesian arrayer.

Example 2

Primer Extension on Chips

The reaction was performed in the vinyl gasket-divided wells on the chip. The volume of the reaction mixture in each well is 10 µL of 1× Klenow fragment buffer (10 mM Tris-HCl, pH 7.5, 5 mM $MgCl_2$, 7.5 mM dithiothreitol) containing 5 units of Klenow fragment of *E coli* polymerase I and 10 nM TAMRA-ddNTP. The extension was carried out at 37° C. for 20 min in the presence of 1 µM of template with TAMRA-ddGTP or in the absence of template with TAMRA-ddTTP. The slides were then washed with a washing buffer (10 mM Tris-HCl, pH 7.5, 150 mM NaCl, 0.05% Tween). The fluorescence images of TAMRA-labeled spots were obtained on GSI Lumonics scanner.

Example 3

Use of a Modified Nucleotide

Figure 2:
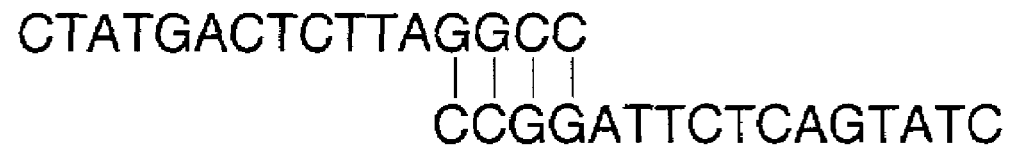
Figure 3:
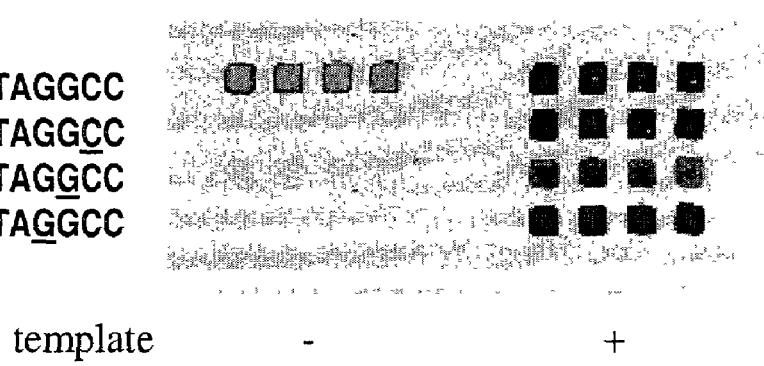
FIG. 3 illustrates primer extension reactions employing modified primers and unmodified 16-mer primers (SEQ ID Nos. 12–14). These 16-mer primers bearing the palindromic sequence 5'-GGCC-3' were used in the primer extension reactions in the absence (−) or presence (+) of template. Array position 1 shows results in the absence of any modification in the primer. Array positions 2 through 4 show results where the primer is modified at the position indicated by the bolded and underscored residue. Template-independent primer extension is inhibited where the modification is at the second, third, or fourth residue from the 3' terminus, which are the third, second, and first residues counting from the 5'-end of the palindromic region in the template strand of the palindrome.

A primer sequence 5'-CTATGACTCTTAGGCC-3' (SEQ ID NO. 10) could form a four-base bridge 5'-GGCC-3' - - - 3'-CCGG-5', which would lead to the incorporation of T in the absence of any template (for example, see FIG. 2). If the primer was modified with a replacement of the 2'-deoxynucleotide near the 3'-terminus by a 2'-methoxy ribonucleotide (2'-MeO-RNA nucleotide), template-independent noise was significantly reduced. But the template-directed signal was not affected by the modification. (see FIG. 3).

Figure 5:
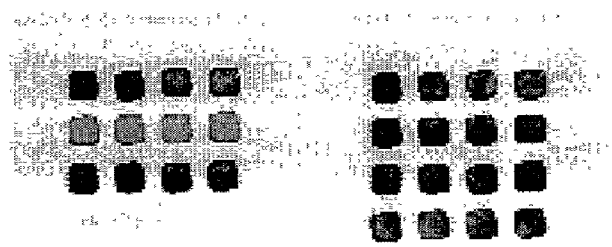
FIG. 5 illustrates primer extension reactions employing modified primers (SEQ ID Nos. 17–19) and unmodified 18-mer primers. Shown are the 18-mer primers having the palindrome-like sequence 5'-GGTACC-3' used in primer extension reactions in the absence (−) or presence (+) of template. Array position 5 shows results in the absence of any modification in the primer. Array positions 6 through 8 show results where the primer is modified at the position indicated by the bold and underscored residue. Template-independent primer extension is inhibited when the modified residue is at the sixth position from the 3'-terminus of the primer, which is the second residue from the 5'-end of the palindrome-like region in the template strand.

Another primer sequence, 5'-CTATGACTCTTAGGTACC-3' (SEQ ID NO. 15) can form a six-base bridge 5'-GGTACC-3' - - - 3'-CCATGG-5', which would also lead to the incorporation of T in the absence of any template (see FIG. 4). In this sequence, the primers having 2'-MeO-RNA at the 5' side of the palindrome GGTACC worked better to prevent template-independent extension than the modifications in the middle of the palindrome. Again none of the modifications affected template-directed extension (see FIG. 5).

Figure 7:
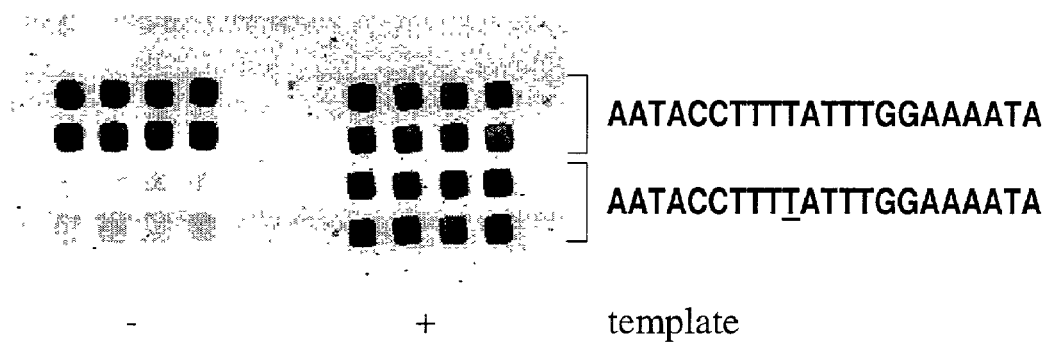
FIG. 7 illustrates primer extension reactions using a 20-mer primer for a SNP with a palindrome-like sequence. Shown are 20-mer primers bearing the palindrome-like sequence 5'-TATTTGGAAAATA-3' that reacts in a primer extension reaction when unmodified (top two rows of array) or modified at the indicated underscored residue, a T at the 13th residue from the 3'-terminus of the primer (SEQ ID No. 22) and the first, or 5'-residue, of the region of palindrome-like sequence (bottom two rows of the array).

As another example, one SNP of interest, having an A/G variation, was showing template-independent noise. The originally designed primer sequence was: 5'-AATACCTTT-TATTTGGAAAATA-3' (SEQ ID NO. 20) (see FIG. 6). It was difficult to resolve the A signal because strong noise existed even in the absence of any template. Secondary structure in this primer may account for this problem. One of the deoxyribonucleotides (T) in the sequence was replaced with a corresponding 2'-MeO-ribonucleotide (2'-MeO-RNA-T) at the 5'-end of the region of secondary structure. The template-independent A signal was significantly reduced (see FIG. 7). Both the original and modified primer AATACCTTT<u>T</u>ATTTGGAAAATA (20 µM) (SEQ ID No. 22) were dissolved in arraying buffer and printed as previously stated. The image indicates that the A noise of the template independent base extension was reduced substantially when the primer was switched from the original to the modified version (see FIG. 7).

In these experiments, the primers showing template-independent noise all have palindrome sequences of four or six bases were designed at the 3'-terminus. Template-independent extension on the terminally bridged primer was blocked when a modified base is placed at or near the 5'-side of the palindrome. Since the modification of 2'-methoxyribonucleotide does not change the base sequence itself, Watson-Crick base-pairing interactions are not expected to be interrupted. Thus, any reduction in primer extension yield may be due to an inhibitory effect of the modified sugar moiety on DNA polymerase activity. In one embodiment of the present invention, the inhibitory effect of the modified sugar is more evident when the modification is in the template strand, as in the case of template-independent extension which is strongly deterred, than when in the primer strand (see FIG. 3, for example).

Example 4

Primer Extension on Microchips

Primer extension on microchips provides a powerful tool for re-sequencing and mini-sequencing a gene of interest. The paradigm platform is a four-color system of alternatively labeled terminating nucleotides, with a different color for each of the four different bases. Typically, on the microchip surface, the size of the spot is as small as possible, in order to achieve high throughput per surface area. Meanwhile, maximal signal intensity should vary directly with the density of the substrate on the surface. Therefore, substrate primers on each single spot are inevitably in close proximity to one another, and the intermolecular interactions between the primers would compete against those (that of the primer and the external template) added during in the assaying reaction. In the case where a complementary sequence of four or more bases exists at the 3'-terminus of the primer, template independent extension can occur with signal strong enough to overwhelm the expected template-directed primer extension, confounding the genotype result. A method that can reduce or eliminate template independent extension represents one important way to ensure that only accurate genotype data is generated. In the examples we use an exogenous nucleotide, modified at the 2'-ribose position, as a replacement for one or more bases in the primer sequence. The inserted exogenous nucleotide at some distance from the 3'-terminus has the ability to inhibit template-independent extension if the primer has a self-complementary sequence at the 3'-terminus, and is therefore able to anneal to a neighbor at the 3'-terminus. The exogenous nucleotide used in this experiment is 2'-methoxyribonucleotide, but is not limited to this particular structure.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows.

What is claimed:

1. A method for inhibiting template independent primer extension, comprising: employing a primer extension reaction using i) a polymerase, ii) a template, iii) a plurality of primers having a palindromic nucleotide sequence, by:
hybridizing a first primer of the plurality of primers to the template so as to form a primer-template duplex;
hybridizing a second of the plurality of primers to a third of the plurality of primers so as to form a primer-primer duplex, and each of the plurality of primers comprise one or more modified nucleotides at or near the 3' or 5' end of the palindromic nucleotide sequence that inhibit(s) template independent primer extension of the primer-primer duplex, wherein the polymerase extends the primer of the primer-template duplex and the one or more modified nucleotides of the plurality of primers is modified at the 2' position and the first, second, and third of the plurality of primers have the same nucleotide sequence.

2. A method according to claim 1, wherein the primer extension reaction is a single nucleotide primer extension reaction.

3. A method according to claim 1, wherein the one or more modified nucleotides comprises an alkoxy group at the 2' position of the nucleotide.

4. A method according to claim 1, wherein the one or more modified nucleotide comprises a methoxy group at the 2' position of the nucleotide.

5. A method according to claim 1, wherein the primers are bound to a solid support.

6. A method according to claim 5, wherein the solid support is an array.

7. A method according to claim 6, wherein the array is an addressable array.

8. A method according to claim 6, wherein the array is a virtual array.

9. A method according to claim 6, wherein the primer comprises a unique tag which comprises a nucleic acid sequence that is capable of hybridizing with a complementary sequence at known positions on the array.

10. A method according to claim 1, wherein the primer extension reaction utilizes one or more chain terminating nucleotides.

11. A method according to claim 10, wherein the one or more chain terminating nucleotides are selected from the group consisting of dideoxynucleotides and acyclonucleotides.

12. A method according to claim 1, wherein the primer extension reaction utilizes at least one labeled nucleotide.

13. A method according to claim 1, wherein the primer has a detectable moiety.

14. A method according to claim 13, wherein the detectable moiety is selected from the group consisting of mass moiety, radioactive moiety, bioluminescent moiety, chemiluminescent moiety, nucleic acid moiety, hapten moiety, enzyme moiety, and fluorescent moiety.

15. A method according to claim 1, wherein the one or more modified nucleotides is at least one nucleotide from the 5' end of the primer.

16. A method according to claim 1, wherein the one or more modified nucleotides is one, two, or three nucleotides from the 5' end of the palindromic nucleotide sequence.

* * * * *

SEQUENCE LISTING

```
<160> NUMBER OF SEQ ID NOS: 22

<210> SEQ ID NO 1
<211> LENGTH: 5
<212> TYPE: DNA
<213> ORGANISM: Artificial Sequence
<220> FEATURE:
<223> OTHER INFORMATION: Synthetic modified primer
<220> FEATURE:
<221> NAME/KEY: misc_feature
<222> LOCATION: (2)...(2)
<223> OTHER INFORMATION: n = 2' methoxy guanosine

<400> SEQUENCE: 1 angcc                                                              5

<210> SEQ ID NO 2
<211> LENGTH: 5
<212> TYPE: DNA
<213> ORGANISM: Artificial Sequence
<220> FEATURE:
<223> OTHER INFORMATION: Synthetic modified primer
<220> FEATURE:
<221> NAME/KEY: misc_feature
<222> LOCATION: (2)...(2)
<223> OTHER INFORMATION: n = 2' methoxy guanosine

<400> SEQUENCE: 2 angcc                                                              5

<210> SEQ ID NO 3
<211> LENGTH: 7
<212> TYPE: DNA
<213> ORGANISM: Artificial Sequence
<220> FEATURE:
<223> OTHER INFORMATION: Synthetic modified primer
<220> FEATURE:
<221> NAME/KEY: misc_feature
<222> LOCATION: (2)...(2)
<223> OTHER INFORMATION: n = 2' methoxy guanosine

<400> SEQUENCE: 3 angtacc                                                            7

<210> SEQ ID NO 4
<211> LENGTH: 7
<212> TYPE: DNA
<213> ORGANISM: Artificial Sequence
<220> FEATURE:
<223> OTHER INFORMATION: Synthetic modified primer
<220> FEATURE:
<221> NAME/KEY: misc_feature
<222> LOCATION: (2)...(2)
<223> OTHER INFORMATION: n = 2' methoxy guanosine

<400> SEQUENCE: 4 angtacc                                                            7
```

```
<210> SEQ ID NO 5
<211> LENGTH: 9
<212> TYPE: DNA
<213> ORGANISM: Artificial Sequence
<220> FEATURE:
<223> OTHER INFORMATION: Synthetic modified primer
<220> FEATURE:
<221> NAME/KEY: misc_feature
<222> LOCATION: (2)...(2)
<223> OTHER INFORMATION: n = 2' methoxy guanosine

<400> SEQUENCE: 5 angtatacc                                                                9

<210> SEQ ID NO 6
<211> LENGTH: 9
<212> TYPE: DNA
<213> ORGANISM: Artificial Sequence
<220> FEATURE:
<223> OTHER INFORMATION: Synthetic modified primer
<220> FEATURE:
<221> NAME/KEY: misc_feature
<222> LOCATION: (2)...(2)
<223> OTHER INFORMATION: n = 2' methoxy guanosine

<400> SEQUENCE: 6 angtatacc                                                                9

<210> SEQ ID NO 7
<211> LENGTH: 12
<212> TYPE: DNA
<213> ORGANISM: Artificial Sequence
<220> FEATURE:
<223> OTHER INFORMATION: Commercially obtained template

<400> SEQUENCE: 7
tgattacggc ct                                                           12

<210> SEQ ID NO 8
<211> LENGTH: 14
<212> TYPE: DNA
<213> ORGANISM: Artificial Sequence
<220> FEATURE:
<223> OTHER INFORMATION: Commercially obtained template

<400> SEQUENCE: 8
tgattacggt acct                                                         14

<210> SEQ ID NO 9
<211> LENGTH: 16
<212> TYPE: DNA
<213> ORGANISM: Artificial Sequence
<220> FEATURE:
<223> OTHER INFORMATION: Commercially obtained template

<400> SEQUENCE: 9
tgattacggt atacct                                                       16

<210> SEQ ID NO 10
<211> LENGTH: 16
<212> TYPE: DNA
<213> ORGANISM: Artificial Sequence
<220> FEATURE:
<223> OTHER INFORMATION: Commercially obtained primer

<400> SEQUENCE: 10
```

```
ctatgactct taggcc                                              16

<210> SEQ ID NO 11
<211> LENGTH: 16
<212> TYPE: DNA
<213> ORGANISM: Artificial Sequence
<220> FEATURE:
<223> OTHER INFORMATION: Commercially obtained primer

<400> SEQUENCE: 11
ctatgactct taggcc                                              16

<210> SEQ ID NO 12
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)...(15)
<223> OTHER INFORMATION: n = 2' methoxy cytosine

<400> SEQUENCE: 12
ctatgactct taggnc                                              16

<210> SEQ ID NO 13
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)...(14)
<223> OTHER INFORMATION: n = 2- methoxy guanosine

<400> SEQUENCE: 13
ctatgactct tagncc                                              16

<210> SEQ ID NO 14
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)...(13)
<223> OTHER INFORMATION: n = 2' methoxy guanosine

<400> SEQUENCE: 14
ctatgactct tangcc                                              16

<210> SEQ ID NO 15
<211> LENGTH: 18
<212> TYPE: DNA
<213> ORGANISM: Artificial Sequence
<220> FEATURE:
<223> OTHER INFORMATION: Commercially obtained primer

<400> SEQUENCE: 15
ctatgactct taggtacc                                            18

<210> SEQ ID NO 16
<211> LENGTH: 18
<212> TYPE: DNA
<213> ORGANISM: Artificial Sequence
```

```
<220> FEATURE:
<223> OTHER INFORMATION: Commercially obtained primer

<400> SEQUENCE: 16
ctatgactct taggtacc                                                18

<210> SEQ ID NO 17
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)...(15)
<223> OTHER INFORMATION: n = 2' methoxy thymidine

<400> SEQUENCE: 17
ctatgactct taggnacc                                                18

<210> SEQ ID NO 18
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)...(14)
<223> OTHER INFORMATION: n = 2' methoxy guanosine

<400> SEQUENCE: 18
ctatgactct tagntacc                                                18

<210> SEQ ID NO 19
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)...(13)
<223> OTHER INFORMATION: n = methoxy guanosine

<400> SEQUENCE: 19
ctatgactct tangtacc                                                18

<210> SEQ ID NO 20
<211> LENGTH: 22
<212> TYPE: DNA
<213> ORGANISM: Artificial Sequence
<220> FEATURE:
<223> OTHER INFORMATION: Commercially obtained primer

<400> SEQUENCE: 20 aataccttttt atttggaaaa ta                                          22

<210> SEQ ID NO 21
<211> LENGTH: 22
<212> TYPE: DNA
<213> ORGANISM: Artificial Sequence
<220> FEATURE:
<223> OTHER INFORMATION: Commercially obtained primer

<400> SEQUENCE: 21 aataccttttt atttggaaaa ta                                          22
```

```
<210> SEQ ID NO 22
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (10)...(10)
<223> OTHER INFORMATION: n = 2' methoxy thymidine

<400> SEQUENCE: 22 aataccttn atttggaaaa ta                                              22
```